(12) United States Patent
Lemon et al.

(10) Patent No.: US 6,290,503 B1
(45) Date of Patent: Sep. 18, 2001

(54) DENTAL CARRIER DEVICE FOR DISPENSING SLURRY-LIKE FILLING MATERIALS

(75) Inventors: Ronald R. Lemon, Metairie, LA (US); Raymond G. Luebke, Cibolo, TX (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/525,153

(22) Filed: Mar. 14, 2000

(51) Int. Cl.[7] .................................................. A61C 5/04
(52) U.S. Cl. ............................. 433/226; 433/80; 433/82
(58) Field of Search ............................... 433/80, 89, 90, 433/141

(56) References Cited

U.S. PATENT DOCUMENTS

| | | | |
|---|---|---|---|
| 860,555 | * 7/1907 | Middaugh | 433/90 X |
| 1,188,417 | * 6/1916 | Dalbey | 433/90 |
| 2,603,871 | * 7/1952 | Call | 433/90 |
| 3,903,605 | 9/1975 | Malmin | 32/40 R |
| 4,306,864 | 12/1981 | Law et al. | 433/83 |
| 4,767,325 | * 8/1988 | Kopunek et al. | 433/90 |
| 4,767,326 | 8/1988 | Bennett et al. | 433/90 |
| 4,798,596 | 1/1989 | Mühlbauer | 604/218 |
| 4,904,437 | 2/1990 | Mühlbauer | 264/295 |
| 4,952,209 | 8/1990 | Mühlbauer | 604/218 |
| 5,067,900 | 11/1991 | McSpadden | 433/81 |
| 5,382,161 | 1/1995 | Roane | 433/81 |
| 5,415,547 | 5/1995 | Torabinejad et al. | 433/228.1 |
| 5,626,473 | 5/1997 | Mühlbauer et al. | 433/89 |
| 5,769,638 | 6/1998 | Torabinejad et al. | 433/228.1 |
| 5,782,633 | 7/1998 | Mühlbauer | 433/90 |
| 5,800,169 | 9/1998 | Mühlbauer | 433/90 |

OTHER PUBLICATIONS

Bates, C.F. et al., "Longitudinal sealing ability of mineral trioxide aggregate as a root–end filling material," Journal of Endodontics, vol. 22, pp. 575–578 (1996).

Luebke, "Affidavit of Raymond G. Luebke," signed on Mar. 8, 2000.

(List continued on next page.)

Primary Examiner—Nicholas D. Lucchesi
(74) Attorney, Agent, or Firm—Bonnie J. Davis; John H. Runnels (57) ABSTRACT

A dental device is disclosed for dispensing a slurry-like dental compound, such as MTA, into a tooth cavity. The device comprises a delivery tool with a dispensing tip and a plastic tubing sleeve, for example, polyethylene, TEFLON®, TYGON®, or other inert tubing. The inner diameter of the sleeve is approximately the same as or slightly less than the outer diameter of the dispensing tip, thereby creating a tight seal between the sleeve and the dispensing tip, but still allowing the sleeve to slide along the dispensing tip when pressure is exerted. The outer diameter of the sleeve is chosen so that the sleeve rim forms a seal around the insertion point on the tooth. The sleeve length is long enough to allow a hydrated filling compound such as MTA to be loaded within the bore of the sleeve between the end of the sleeve and the displacing shaft, but short enough to withstand pressure applied to the dispensing tip to extrude the compound. Additionally, the plastic sleeve can be cut to a desired length or angle, which maximizes the flexibility of effective delivery of filling material in tight places, for example, at the root tip. The size of the dental device depends on its intended use, e.g., a smaller size for retrograde or micro-surgical fillings, e.g., root canals. The dispensing tip can be angled to facilitate dispensing the filling material in various places within the mouth. The dental device can also be adapted to attach to a vibration source, either mechanical, sonic, or ultrasonic, to aid in condensing the filling material by aiding the escape of air pockets. In an alternative embodiment, the sleeve has minute pores in the tubing and is pre-loaded with the dehydrated filling material. When the sleeve end of the dental device is placed in water, water enters the pores of the sleeve and hydrates the filling material.

21 Claims, 6 Drawing Sheets

OTHER PUBLICATIONS

Material Safety Data Sheet: ProRoot™ MTA (Mineral Trioxide Aggregate) Root Canal Repair Material; Dentsply Tulsa Dental, Tulsa, Oklahoma.

Product Insert: ProRoot™ MTA (Mineral Trioxide Aggregate) Root Canal Repair Material; Dentsply Tulsa Dental, Tulsa, Oklahoma.

Torabinejad, M. et al., "Cytotoxicity of four root end filling materials," Journal of Endodontics, vol. 21, pp. 489–492 (1995).

Torabinejad, M. et al., "Dye leakage of four root end filling materials: Effects of blood contamination," Journal of Endodontics, vol. 20, pp. 159–163 (1994).

Torabinejad, M. et al., "Histologic assessment of mineral trioxide aggregate as a root–end filling in monkeys," Journal of Endodontics, vol. 23, pp. 225–228 (1997).

Torabinejad, M. et al., "Investigation of mineral trioxide aggregate for root–end filling in dogs," Journal of Endodontics, vol. 21, pp. 603–608 (1995).

Torabinejad, M. et al., "Physical and chemical properties of a new root–end filling material," Journal of Endodontics, vol. 21, pp. 349–353 (1995).

Torabinejad, M. et al., "Sealing ability of a mineral trioxide aggregate when used as a root–end filling material," Journal of Endodontics, vol. 19, pp. 591–595 (1993).

Torabinejad, M. et al., "Tissue reaction to implanted root–end filling materials in the tibia and mandible of guinea pigs," Journal of Endodontics, vol. 24, pp. 468–471 (1998).

* cited by examiner

DENTAL CARRIER DEVICE FOR DISPENSING SLURRY-LIKE FILLING MATERIALS

This invention pertains to a dental device for dispensing a slurry-like filling material into a tooth cavity, including a root canal, comprising a plastic sleeve which contains the filling material and a dispensing tip for pushing the filling material into the cavity. The plastic sleeve also forms a seal around the cavity to be filled and prevents undesirable extrusion of filling material onto the surrounding tissues.

Dentists and endodontists use various materials to fill surgically prepared cavities or to seal spaces within a tooth. The consistency of the filling material is highly variable. For example, silver amalgam is a liquid metal of high density which is compressed into the cavity with force. Gutta percha is a rubber material, which is usually heated to increase its plasticity before placing into the cavity. Others, e.g., cements based on zinc oxide eugenol, are viscous and capable of flowing into the cavity. The choice of filling material and dispenser depends on the size and placement of the cavity that needs to be filled. In an orthograde filling process, the tooth cavity is filled through the crown area of the tooth, usually into a relatively large area. In a retrograde filling process, where the tooth is filled through the root-tip area, the surgical opening in the gum and bone to expose the root and the root-tip canal is smaller and requires a precise filling technique.

An effective filling material exhibits various qualities, such as adhering to the walls of the cavity, compatibility with the surrounding tissue, and suitability for moist environments. In a retrograde filling process, biocompatibility is even more important. A filling material that will allow natural tooth tissue, cementum, to grow will more fully protect the root area from bacteria. Many filling materials are not effective as a retrograde filling material because they are not tissue-compatible. For example, amalgam, a commonly used retrograde filling material, does not allow the growth of cementum and allows leakage due to its poor adaptation to the dentinal cavity walls. Amalgam has been shown to corrode after exposure to moisture over time. The zinc oxide eugenol-based cements are moisture-sensitive, irritate tissues, and clinically are difficult to handle.

A new generation filling material that has shown to be more biocompatible is Mineral Trioxide Aggregate ("MTA"), for example ProRoot™ MTA (Dentsply Tulsa Dental, Tulsa, Okla.), described in U.S. Pat. Nos. 5,415,547 and 5,769,638. MTA is useful for both orthograde and retrograde filling. MTA is similar to Portland cement and comprises fine hydrophilic particles of tricalcium silicate, tricalcium aluminate, and tricalcium oxide, which set in the presence of water into a colloidal gel. MTA is packaged as a dry powder and, with the addition of water, forms a slurry with a putty-like consistency, which normally hardens within 4 to 5 hours. MTA is used in a wide variety of dental applications, including as pulp capping material, as root-end filling material, in orifice sealing, in fracture sealing, as repair of root canals as an apical plug, and as repair of root perforations during root canal therapy. See M. Torabinejad et al., "Physical and chemical properties of a new root-end filling material," Journal of Endodontics, vol. 21, pp. 349–353 (1995). The density of MTA can be increased by tapping the filling material to remove trapped air bubbles and to settle the silica particles. Although MTA is not itself radiopaque, a radiopaque component, for example, bismuth oxide ($Bi_2O_3$), may be added for diagnostic purposes.

The eventual hardening of MTA is not as affected by moisture and blood as are other filling materials. Instead, moisture assists in the hydration reactions responsible for hardening. Additionally, MTA is biocompatible, allowing cementum to grow and increase the seal against bacteria around the tooth. See M. Torabinejad et al., "Tissue reaction to implanted root-end filling materials in the tibia and mandible of guinea pigs," Journal of Endodontics, vol. 24, pp. 468–471 (1998); M. Torabinejad et al., "Histologic assessment of mineral trioxide aggregate as a root-end filling in monkeys," Journal of Endodontics, vol. 23, pp. 225–228 (1997); C. F. Bates et al., "Longitudinal sealing ability of mineral trioxide aggregate as a root-end filling material," Journal of Endodontics, vol. 22, pp. 575–578 (1996); M. Torabinejad et al., "Investigation of mineral trioxide aggregate for root-end filling in dogs," Journal of Endodontics, vol. 21, pp. 603–608 (1995); M. Torabinejad et al., "Cytotoxicity of four root end filling materials," Journal of Endodontics, vol. 21, pp. 489–492 (1995); M. Torabinejad et al., "Dye leakage of four root end filling materials: Effects of blood contamination," Journal of Endodontics, vol. 20, pp. 159–163 (1994); and M. Torabinejad et al., "Sealing ability of a mineral trioxide aggregate when used as a root-end filling material," Journal of Endodontics, vol. 19, pp. 591–595 (1993).

The primary problem with MTA has been the lack of an effective method to dispense MTA into a tooth cavity. Currently, MTA is applied, by necessity, with dental devices designed to apply other filling materials with different consistencies, such as gutta percha, amalgam, and viscous zinc oxide eugenol cements. These devices do not satisfactorily dispense MTA into a tooth cavity because they often cause an overflow of MTA. For example, the amalgam devices are designed to deliver a set amount of the dense amalgam when sufficient pressure is applied. MTA is less dense and more fluid than amalgam and is delivered much faster than amalgam by the same device. MTA often overfills the cavity and spills into surrounding tissues. The devices designed for the more viscous cements are usually based on a syringe design. These devices become clogged with the slurry-like MTA because the insoluble particles become lodged in the small bore of the syringe. Many also present sterilization problems. Moreover, none of the current devices are of a design that would allow the formation of a seal between the dispenser and the tooth; a seal that would prevent the MTA from extruding into the surrounding tooth area.

U.S. Pat. No. 5,382,161 describes a prefilled, disposable apparatus for placing a thermoplastic material (e.g. gutta percha) into an endodontically-prepared root canal. The apparatus comprises a displacing shaft and a carrier tip of a hollow segment of cylindrical tubing made of thermoconducting material, preferably stainless steel hypodermic needle tubing. After heating the carrier to soften the thermoplastic filling material, the carrier tip is inserted inside the prepared root canal, and the material is advanced by exerting pressure on the displacing shaft. The stickiness of the heated filling material holds the displacing shaft in the carrier and also forms a seal between the displacing shaft and the carrier.

U.S. Pat. No. 5,067,900 describes another apparatus for applying gutta percha. The apparatus can be heated to pre-soften the gutta percha before inserting into the tooth.

U.S. Pat. No. 3,903,605 describes the use of an electrical, manual, or ultrasonic instrument to heat, condense, and pack gutta percha into a root canal; and the use of ultrasonically-activated tips to place filling material into tooth cavities. U.S. Pat. No. 4,306,864 describes a dental implement for dispensing amalgam. The implement includes a handle with at least one amalgam dispenser and a plugger corresponding to each amalgam dispenser for condensing the amalgam dispensed. Each amalgam dispenser consists of a hollow carrier made of metal, a dispensing rod, and a lever mechanism. The amalgam carrier is raised by depressing the lever mechanism, which causes a portion of the dispensing rod to extend beyond the end of the amalgam carrier, thus dispensing all the amalgam into the tooth cavity.

U.S. Pat. No. 4,767,326 describes a device which consists of a cartridge having a tubular body, a piston and a discharge nozzle. Once the filling material is loaded into the cartridge, the cartridge is mounted on an ejector-type holder. The filling material is advanced through the discharge nozzle by exerting pressure on the piston.

The following patents describe devices, usually based on a syringe-styled action, that are used for dispensing more fluid filling materials.

U.S. Pat. No. 5,800,169 describes a device for delivering and metering viscous dental compounds. The device consists of a piston, a piston rod, and a cylindrical syringe capsule. The compound is loaded into the syringe capsule and is advanced through a tubular nozzle by exerting pressure on the piston rod, which in turn exerts pressure on the piston in the syringe capsule.

U.S. Pat. No. 5,782,633 describes a dental compound applicator having a flexible ram, a pusher rod, a first rack member, a second rack member, and a gear reduction mechanism. A syringe containing the dental compound and a plunger mechanism can be connected to the applicator.

U.S. Pat. No. 5,626,473 describes a dental compound applicator having a shaft that may be gripped in a pencil-hold fashion. The shaft is connected to a syringe containing a viscous material and a plunger. The material is advanced by rotating a wheel around a fixed axis by using the index finger of the gripping hand.

U.S. Pat. Nos. 4,952,209, 4,904,437, and 4,798,596 describe a disposable applicator syringe for a dental compound having a tubular structure, a gripping flange and a rod-like piston. The syringe tubular structure tapers to a thin discharge tube. The syringe is meant for once-only use.

Clinical experience has shown that none of these prior devices are well suited to handle the unique characteristics of the slurry-like MTA, especially for application of small amounts in a root-tip canal. There is an unfilled need for an inexpensive device that can effectively deliver slurry-like materials into tooth cavities, especially the small root-tip canals, by controlling the amount of compound to be delivered and preventing extrusion into the surrounding tissues.

We have discovered a dental device for dispensing a slurry-like dental compound, such as MTA, into a tooth cavity. The device comprises a delivery tool with a dispensing tip and a plastic tubing sleeve, for example, polyethylene, TEFLON®, TYGON®, or other inert tubing. The inner diameter of the sleeve is approximately the same as or slightly less than the outer diameter of the dispensing tip, thereby creating a tight seal between the sleeve and the dispensing tip, but still allowing the sleeve to slide along the dispensing tip when pressure is exerted. The outer diameter of the sleeve is chosen so that the sleeve rim forms a seal around the insertion point on the tooth. The sleeve length is long enough to allow a hydrated filling compound such as MTA to be loaded within the bore of the sleeve between the end of the sleeve and the displacing shaft, but short enough to withstand the pressure applied to the dispensing tip to extrude the compound. Additionally, the plastic sleeve can be cut to a desired length or angle, which maximizes the flexibility of effective delivery of filling material in tight places, for example, at the root tip. The size of the dental device depends on its use, e.g., a smaller size for retrograde or micro-surgical fillings, e.g., root canals. The dispensing tip can be angled to facilitate dispensing the filling material in various places within the mouth. The dental device can also be adapted to attach to a vibration source, either mechanical, sonic, or ultrasonic, to aid in condensing the filling material by aiding the escape of air pockets. In an alternative embodiment, the sleeve has minute pores in the tubing and is pre-loaded with the dehydrated filling material. When the sleeve end of the dental device is placed in water, water enters the pores of the sleeve and hydrates the filling material.

We have discovered a dental device that effectively dispenses filling material of a slurry-like consistency to a tooth cavity without extruding filling material into surrounding areas of the tooth. This device comprises a delivery tool with a dispensing tip and a tubular sleeve. When the sleeve is filled with filling material and placed on the tooth, the dispensing tip is forced down into the sleeve thus dispensing filling material into the tooth. The novel device allows the dentist or endodontist to form a tight seal between the tooth and the sleeve, which minimizes leakage of compound into the area around the tooth cavity. This tight seal results from the flexibility and the wall thickness of the plastic tubular sleeve. This seal also creates a back pressure that signals the dentist that the tooth cavity is full and prevents the dentist or endodontist from overfilling the tooth cavity. Thus the device allows for greater control in dispensing this type of filling material than the control from currently used devices. Moreover, the dental device, especially for retrograde filling, can be adapted to attach to a vibration source, either mechanical, sonic, or ultrasonic. The mechanical vibration in the tip makes the MTA a denser material. The vibration settles the insoluble particles and releases air pockets.

Although this dental device is useful for many purposes, FIGS. 1–4 illustrate using the dental device for retrograde filling in a root-end canal, a particularly difficult procedure because of the location and of the small size. FIGS. 1a–1c illustrate the preparation of the root-end canal, after the root has been exposed by surgery through the gum and bone. FIG. 1a illustrates a typical tooth with a crown 2 and a root 4. FIG. 1b illustrates re-section of the root with a surgical bur 6. Then a root-end canal 10 is prepared to a certain depth, usually between about 3 mm and 5 mm. This canal is usually made using an ultrasonic cutting tip 8.

Figures 1A, 1B, 1C:
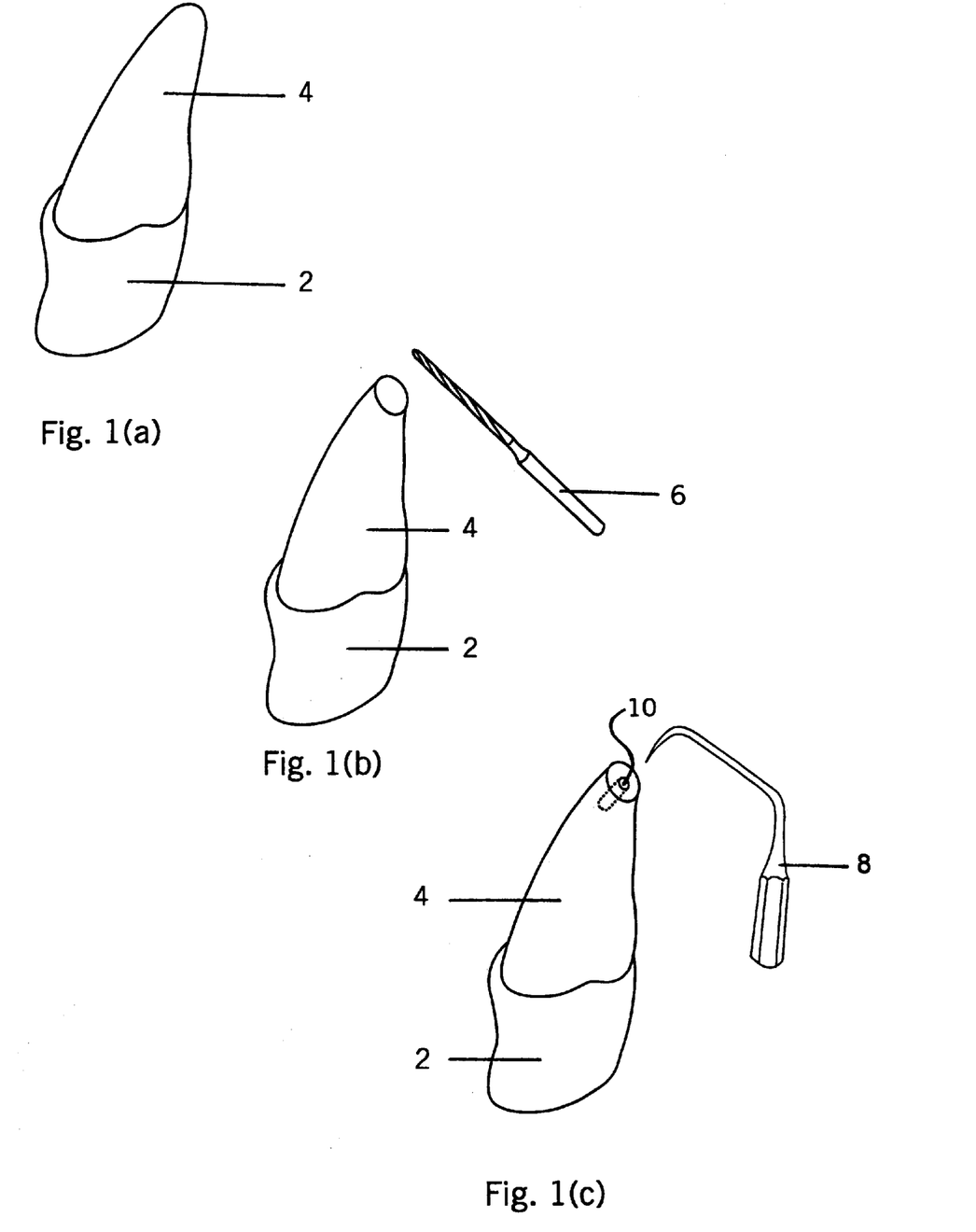
FIGS. 1a–1c illustrate the endodontic surgical preparation of a root-tip canal prior to dispensing a filling material.
Figure 2A:
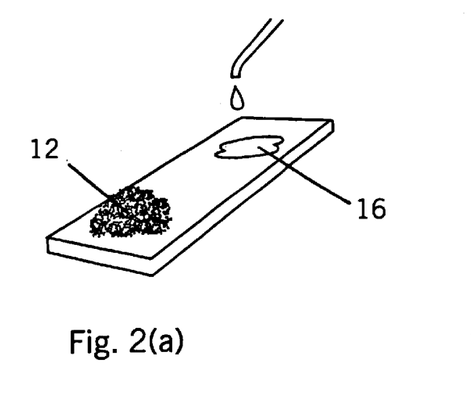
FIGS. 2a–2d illustrate one embodiment of the sleeve of the dental device in which the filling material is first hydrated and then loaded into the sleeve attached to a dispensing tip.
Figure 2B:
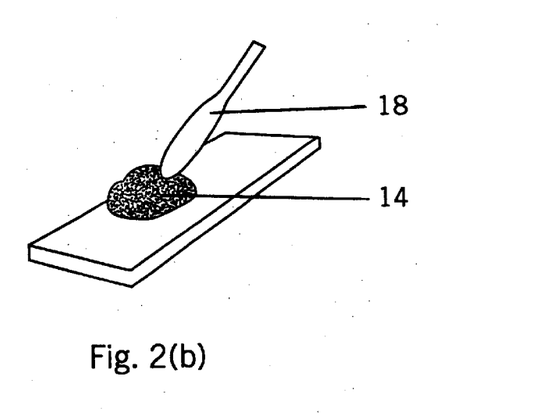
Figure 2C:
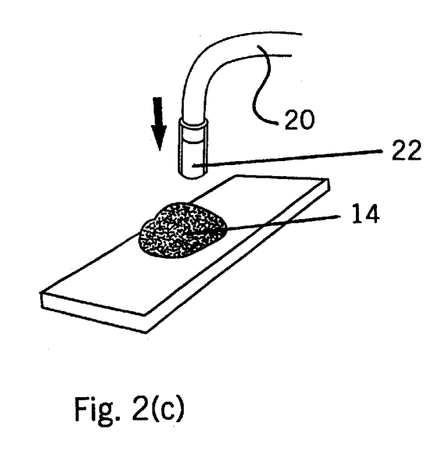
Figure 2D:
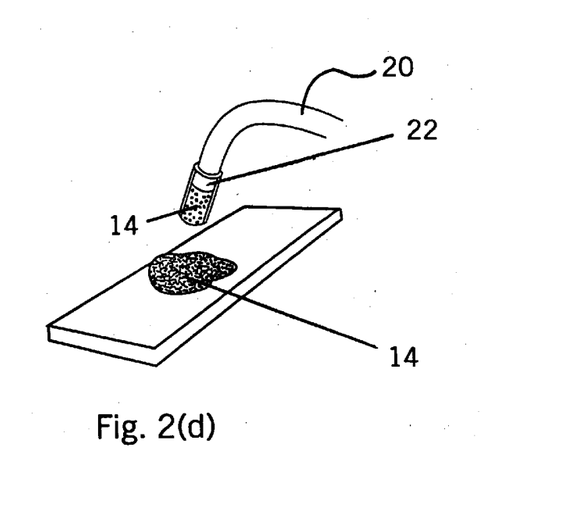

FIGS. 2a–2d illustrate one embodiment of the dental device. In this embodiment, the filling material 12 is first hydrated with liquid 16 (water, in the case of MTA) and mixed with a standard dental spatula 18. The hydrated filling material 14 is then ready to load into an empty sleeve. FIG. 2c illustrates an empty sleeve 22 on a dispensing tip 20. Sleeve 22 is then filled manually by pressing the hydrated filling material 14 into the sleeve 22. A sleeve 22 loaded with hydrated filling 14 is shown in FIG. 2d.

Figures 3A, 3B, 3C:
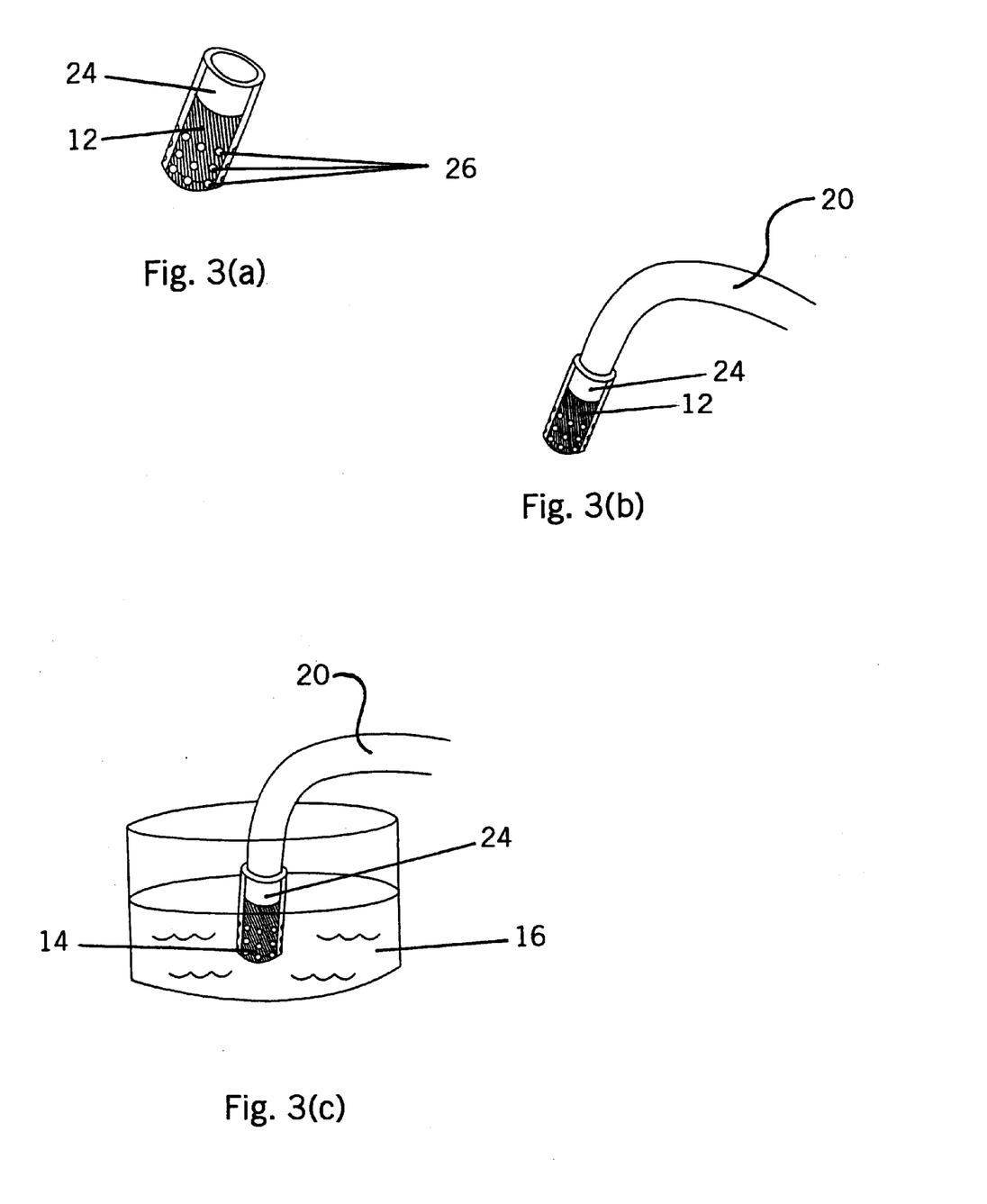
FIGS. 3a–3c illustrate another embodiment of the sleeve of the dental device in which the perforated sleeve is prefilled with dehydrated filling material which can be hydrated by placing the sleeve in liquid.

FIGS. 3a–3c illustrate an alternative embodiment. In this embodiment, as shown in FIG. 3a, a plastic sleeve 24, e.g., one made from polyethylene tubing, with small perforations 26 (a diameter between about 0.1 mm and about 0.6 mm) is pre-filled with dehydrated filling material 12. This sleeve will have a cap on the end to keep the dry material inside the sleeve (not shown). Sleeve 24 is placed on dispensing tip 20 and then placed in hydrating liquid 16, such as water. The liquid 16 travels through pores 26 in sleeve 24 to hydrate filling material 12 inside. The cap is then removed and sleeve 22 with hydrated filling material 14 is ready for use.

Figure 4A:
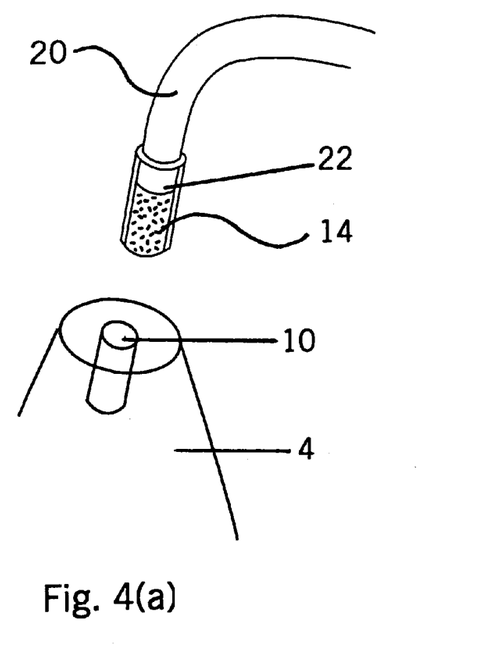
FIGS. 4a–4c illustrate dispensing the filling material into a prepared tooth canal using the dental device.
Figure 4B:
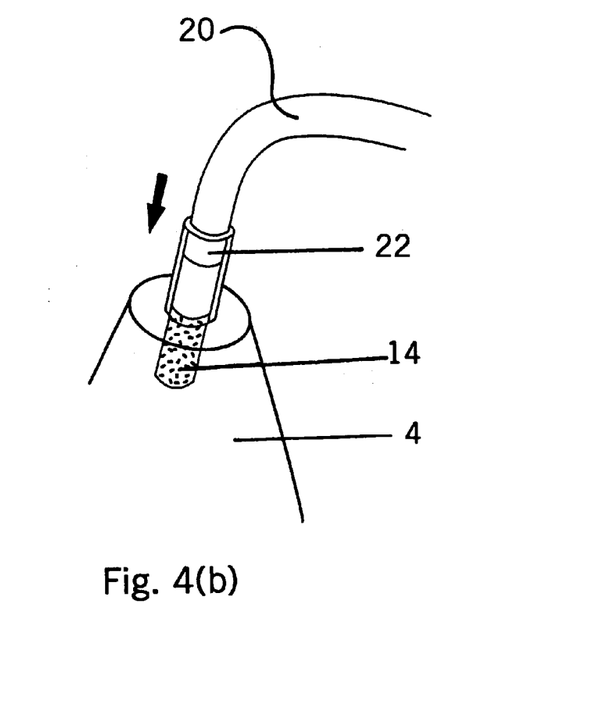
Figure 4C:
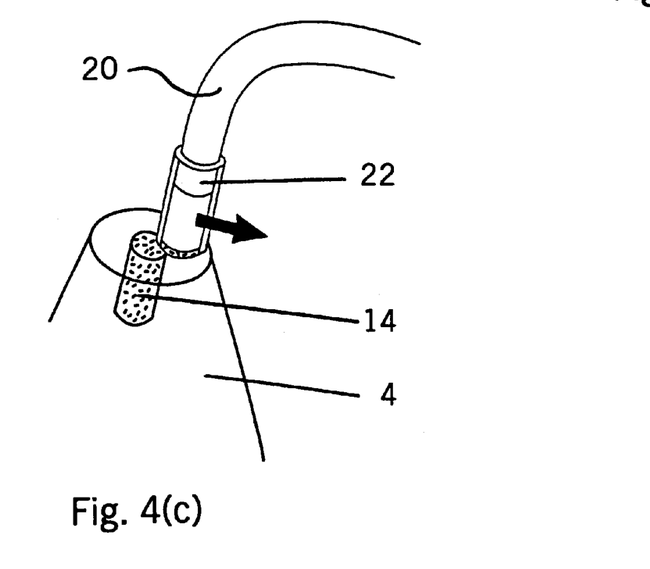

FIGS. 4a–4c illustrate the use of either of the above embodiments of the dental device. Dispensing tip 20 can be an extension of a hand-held tool, or it may be a tool connected to a vibration generating device that is either mechanical, sonic, or ultrasonic. Once sleeve 22 is loaded with hydrated filling material 14, dispensing tool 20 is used to place sleeve 22 around the entry to root-tip canal 10, as shown in FIG. 4a. Downward pressure is then manually applied to dispensing tip 20, as shown in FIG. 4b, to move the tip relative to sleeve 22, a movement which forces hydrated filling material 14 into root-end canal 10. Once root-end canal 10 is filled, back pressure is created because of the seal between sleeve 22 on tooth root 4, and the seal between sleeve 22 and dispensing tip 20. This back pressure is a signal to stop dispensing filling material 14 and to move the sleeve 22 horizontally across the root tip 4 to clean the area, as illustrated in FIG. 4c. Thus the root-tip cavity 10 is filled with little or no extrusion of excess filling material.

Although FIGS. 4a–4c illustrate a dispensing tip 20 with a solid sleeve 22, a similar method could be used with a perforated sleeve 24, as shown in FIGS. 3a–3c. The perforations 26 are not so large as to allow hydrated filling material 14 to escape when pressure is exerted by dispensing rod 20, e.g., perforations of about 1 mm diameter.

Figure 5:
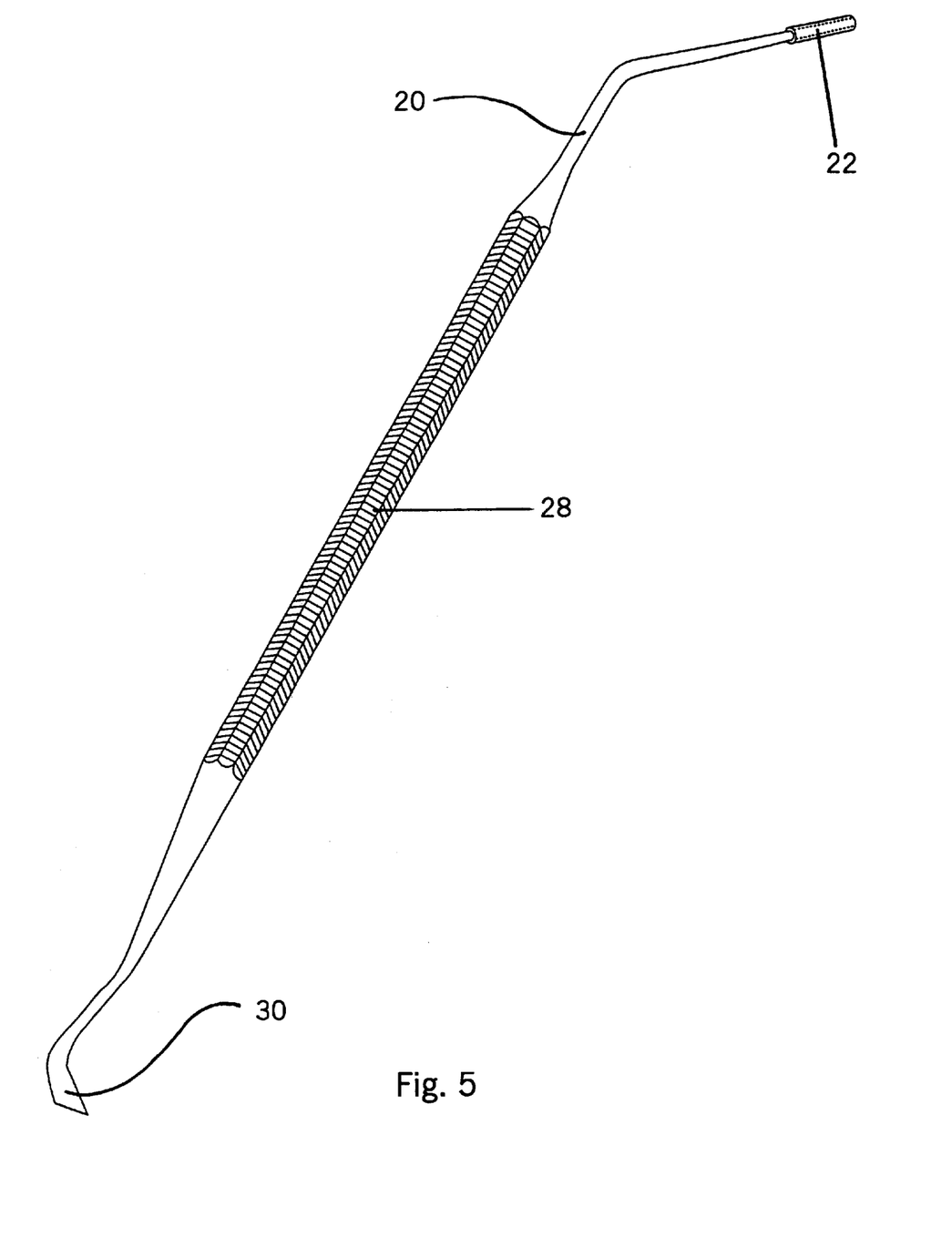
FIG. 5 illustrates one embodiment of the dental device with a sleeve attached to an extended dispensing tip of a hand tool, showing the holding shaft of the device, and a different tip on the other end of the holding shaft for condensing and carving the filling material once placed in the tooth cavity.

FIG. 5 illustrates a type of dental hand tool that features a dispensing tip 20 with a sleeve 22. The tool has shaft 28 for grasping and applying pressure to dispensing tip 20. Optionally, the tool could also have a different tip for the other end, shown here to be a condensing and carving tip 30. Dispensing tip 20 in FIG. 5 is shown as an extended tip, useful for general orthograde filling in the mouth.

Figure 6A:
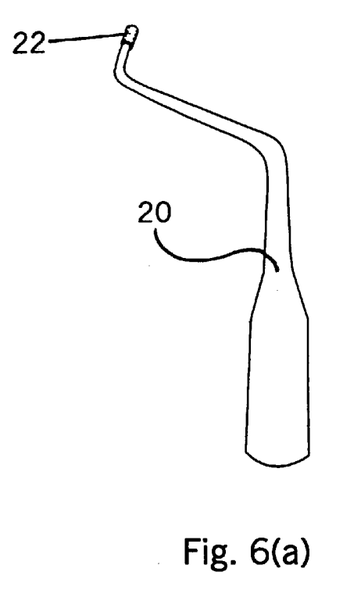
FIGS. 6a–6c illustrate several embodiments of dispensing tips that can be used to dispense the filling material in various places in the mouth.
Figure 6B:
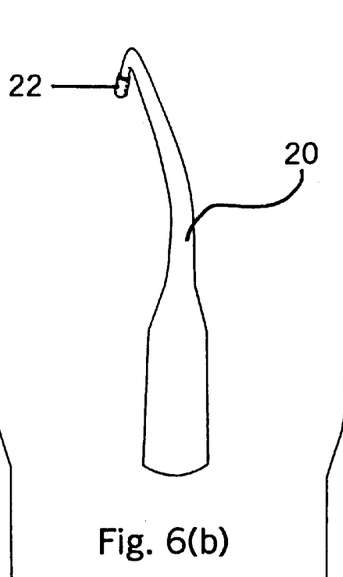
Figure 6C:
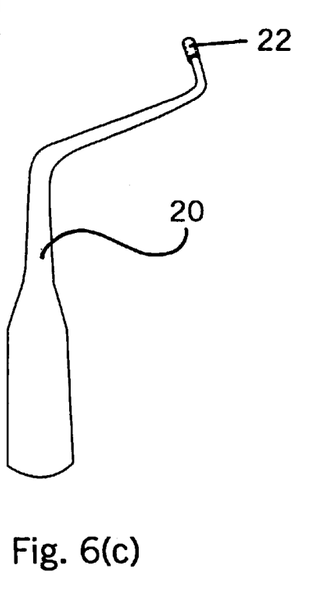

FIGS. 6a–6c illustrate examples of other potential shapes for dispensing tips that are made to attach to a vibration source, e.g., P5 Booster Suprasson, Satelec-Amadent/American Medical & Dental Corp (Cherry Hill, N.J.). FIG. 6a illustrates a tip useful for accessing the left side of the mouth; FIG. 6b, a right angle tip for access to the root tips of front teeth; and FIG. 6c, a tip for accessing the right side of the mouth. The tips shown in FIGS. 6a–6c mimic the angle and size of the common cutting tips used in microsurgery to gain access to the root-tips of various teeth.

The size of the sleeve and dispensing tip depend on the intended use. For use in orthograde filling, the inner diameter of the sleeve could be between about 3 mm to about 6 mm, with a dispensing tip diameter to match. For retrograde filling, smaller sleeves and tips are required with a range of inner diameter between about 2 mm and about 4 mm. The outer diameter is chosen so that a good seal can be made with the tooth surrounding the cavity. The length of the sleeve may be from between about 4 mm and about 10 mm. The sleeve can be made of any inert, plastic tubing, preferably transparent, for example, polyethylene, TEFLON®, or TYGON®. The sleeve material must be flexible enough to create a seal with the tooth.

The dispensing tip may made of any material that can be sterilized and that is strong enough to withstand the pressure necessary to dispense the filling material from the sleeve, e.g., surgical steel. The size and shape of the tip can be adapted to almost any application for dispensing filling material. Moreover, the dispensing tip, particularly for retrograde filling, could be adapted to be placed on a vibration source, either mechanical, sonic, or ultrasonic, to aid in dispensing and condensing the material by removing air pockets and settling the particles.

EXAMPLE 1

Hydration of MTA inside the Sleeve

To confirm that dehydrated MTA can be adequately hydrated inside a porous sleeve, ten plastic sleeves (5 mm in length and 3 mm in diameter) were cut from polyethylene IV tubing (APIO-1, American Dental Manufacturing Company, Missoula, Mont.). Five of the sleeves were perforated with a pin with a tip of 0.5 mm tip to produce six holes equally spaced around each sleeve. The five sleeves without perforations were filled with MTA that was hydrated using the manufacturer's directions using a spatula until a colloidal gel was formed. The five perforated sleeves were filled with dehydrated MTA as packaged by Dentsply Tulsa Dental (Tulsa, Okla.). See "ProRoot™ MTA (Mineral Trioxide Aggregate) Root Canal Repair Material," Pamphlet with directions for use, No. DF1098, Dentsply Tulsa Dental, Tulsa, Okla. Then each of these sleeves was placed in a water bath for 7 sec. Once filled, all sleeves were attached to a hand-held condenser (AP 10 2R, #LE 0685; American Dental Manufacturing Company, Missoula, Mont.) with a 3 mm diameter tip. All samples were then extruded into individual wells in a plastic sample box. The samples were then covered with wet gauze and stored for one week at 100% humidity. After storage, the samples were tested for hardness by scratching the surface with a dental excavator (31L excavator; Moyco Union Broach, York, Pa.). There was no observable difference in hardness between the samples hydrated by spatulation and those hydrated inside the sleeve.

This experiment demonstrated that MTA powder placed inside a sleeve with pores can be hydrated by placing the sleeve in water for a sufficient time. Under these conditions, spatulation with water was not required for MTA to form a colloidal gel and harden properly.

The complete disclosures of all references cited in this specification are hereby incorporated by reference. In the event of an otherwise irreconcilable conflict, however, the present specification shall control.

We claim:

1. A method for dispensing a filling material into a cavity in a tooth, without extruding a substantial amount of the material into surrounding areas of the tooth, said method comprising the steps of:

(a) positioning on the tooth surface surrounding the cavity a dental apparatus comprising a dispensing tip and a polymer sleeve; wherein the sleeve comprises a proximal end, a distal end, and a bore containing the filling material; wherein the proximal end is fitted snugly around the dispensing tip; and wherein a seal is formed between the distal end and the surface of the tooth around the cavity;

(b) exerting pressure on the dispensing tip in a direction toward the cavity, so that the dispensing tip moves downward in the sleeve and forces at least some of the filling material from the sleeve into the tooth cavity until the tooth cavity is filled with the filling material; and (c) releasing the pressure when back-pressure from the filling material in the cavity indicates that the cavity is filled.

2. A method as recited in claim 1, wherein the dispensing tip comprises a hand-held tool.

3. A method as recited in claim 1, wherein the dispensing tip is attached to a vibration-generating device.

4. A method as recited in claim 1, wherein the sleeve comprises a transparent polymer.

5. A method as recited in claim 1, wherein the sleeve additionally comprises a wall with perforations, wherein the wall holds dehydrated filling material inside the sleeve; wherein said method additionally comprises the step of placing the sleeve into liquid to hydrate the filling material before said positioning step.

6. A method as recited in claim 1, wherein the sleeve has a length between about 4 mm and about 10 mm.

7. A method as recited in claim 1, wherein the sleeve has an inner diameter between about 2 mm and about 6 mm.

8. A method as recited in claim 1, wherein the filling material comprises mineral trioxide aggregate.

9. An apparatus for storing a dehydrated filling material, and dispensing a hydrated filling material into a tooth cavity, without extruding a substantial amount of the material into surrounding areas of the tooth, said apparatus comprising:

(a) a dispensing tip; and (b) a polymer sleeve comprising a proximal end and a distal end, wherein said proximal end is fitted snugly around said dispensing tip; wherein said sleeve additionally comprises a wall with perforations, wherein said wall holds the dehydrated filling material inside said sleeve; wherein the perforations are large enough to allow the entry of liquid into said sleeve, without allowing leakage of the filling material; and wherein said distal end is adapted to form a seal with the tooth surface around the cavity;

and wherein:

(c) said apparatus is adapted to be positioned on the tooth surface surrounding the cavity such that when pressure is exerted on said dispensing tip in a direction toward the cavity, said dispensing tip will move downward in the sleeve and force at least some of the filling material from said sleeve into the tooth cavity until the tooth cavity is filled with the filling material.

10. An apparatus as recited in claim 1, wherein said dispensing tip comprises a hand-held tool.

11. An apparatus as recited in claim 10, wherein said dispensing tip is attached to a vibration-generating device.

12. A n apparatus as recited in claim 10, wherein said sleeve comprises a transparent polymer.

13. An apparatus as recited in claim 10, wherein said sleeve has a length between about 4 mm and about 10 mm.

14. An apparatus as recited in claim 10, wherein said sleeve has an inner diameter between about 2 mm and about 6 mm.

15. An apparatus as recited in claim 10, wherein said filling material comprises mineral trioxide aggregate.

16. An apparatus for storing a dehydrated filling material, and dispensing a hydrated filling material into a tooth cavity, said apparatus comprising:

(a) dehydrated filling material suitable for filling a tooth cavity; and (b) a polymer sleeve comprising a proximal end and a distal end, wherein said proximal end is adapted to fit snugly around a dispensing tip; wherein said sleeve additionally comprises a wall with perforations, wherein the wall holds said dehydrated filling material inside the sleeve; and wherein the perforations are large enough to allow the entry of liquid into said sleeve.

17. An apparatus as recited in claim 16, wherein said sleeve comprises a transparent polymer.

18. An apparatus as recited in claim 16, wherein said sleeve has a length between about 4 mm and about 10 mm.

19. An apparatus as recited in claim 16, wherein said sleeve has an inner diameter between about 2 mm and about 6 mm.

20. An apparatus as recited in claim 16, wherein said filling material comprises mineral trioxide aggregate.

21. An apparatus as recited in claim 16, wherein said distal end of said plastic sleeve is adapted to form a seal with the tooth surface around the tooth cavity.

* * * * *